United States Patent
Hölzer et al.

(10) Patent No.: US 11,935,230 B2
(45) Date of Patent: Mar. 19, 2024

(54) AI-BASED IMAGE ANALYSIS FOR THE DETECTION OF NORMAL IMAGES

(71) Applicant: Siemens Healthineers AG, Forchheim (DE)

(72) Inventors: Philipp Hölzer, Plainsboro, NJ (US); Richard Frank, Alexandria, VA (US); Sebastian Schmidt, Weisendorf (DE); Jonathan Sperl, Bamberg (DE)

(73) Assignee: Siemens Healthineers AG, Forchheim (DE)

( * ) Notice: Subject to any disclaimer, the term of this patent is extended or adjusted under 35 U.S.C. 154(b) by 416 days.

(21) Appl. No.: 17/237,160

(22) Filed: Apr. 22, 2021

(65) Prior Publication Data

US 2021/0383174 A1    Dec. 9, 2021

Related U.S. Application Data

(60) Provisional application No. 63/033,875, filed on Jun. 3, 2020.

(51) Int. Cl.
*G06K 9/62*    (2022.01)
*G06F 18/21*    (2023.01)
(Continued)

(52) U.S. Cl.
CPC ........ *G06T 7/0012* (2013.01); *G06F 18/2163* (2023.01); *G06F 18/2433* (2023.01);
(Continued)

(58) Field of Classification Search
CPC ......... G06T 7/0012; G06T 2207/20081; G06T 2207/20084; G06T 2207/30096;
(Continued)

(56) References Cited

U.S. PATENT DOCUMENTS

2017/0372007 A1   12/2017   Lu et al.
2018/0060512 A1   3/2018    Sorenson et al.
(Continued)

FOREIGN PATENT DOCUMENTS

CN     107004043 A    8/2017
CN     109074500 A    12/2018
(Continued)

OTHER PUBLICATIONS

Chakravarty, Arunava, Divya Jyothi Gaddipati, and Jayanthi Sivaswamy. "Construction of a retinal atlas for macular oct volumes." Image Analysis and Recognition: 15th International Conference, ICIAR 2018, Póvoa de Varzim, Portugal, Jun. 27-29, 2018, Proceedings 15. Springer International Publishing, 2018.
(Continued)

*Primary Examiner* — Jerome Grant, II

(57) ABSTRACT

A system and method for identifying abnormal medical images. The system can be configured to receive a medical image, segment an anatomical structure from the medical image to define a segmented dataset, register the segmented dataset to a baseline dataset defining a normal anatomical structure, classify, by an abnormality classifier, whether the anatomical structure within the medical image as either abnormal or normal, wherein the abnormality classifier comprises a machine learning algorithm trained to distinguish between normal and abnormal versions of the anatomical structure in medical images, and based on whether the anatomical structure can be segmented from the medical image, whether the segmented dataset can be registered to the baseline dataset, or a classification associated with the medical image output by the abnormality classifier, flagging the medical image as either normal or abnormal.

11 Claims, 3 Drawing Sheets

(51) Int. Cl.
   *G06F 18/2433* (2023.01)
   *G06N 5/04* (2023.01)
   *G06N 20/00* (2019.01)
   *G06T 7/00* (2017.01)
   *G16H 30/20* (2018.01)
   *G16H 30/40* (2018.01)
   *G16H 40/20* (2018.01)

(52) U.S. Cl.
   CPC ............... *G06N 5/04* (2013.01); *G06N 20/00* (2019.01); *G16H 30/20* (2018.01); *G16H 30/40* (2018.01); *G16H 40/20* (2018.01); *G06V 2201/03* (2022.01)

(58) Field of Classification Search
   CPC . G06T 7/11; G06T 7/136; G06T 2207/30004; G06F 18/2163; G06F 18/2433; G06F 18/241; G06N 5/04; G06N 20/00; G16H 30/20; G16H 30/40; G16H 40/20; G06V 2201/03
   USPC .......................................................... 382/128
   See application file for complete search history.

(56) References Cited

U.S. PATENT DOCUMENTS

| | | |
|---|---|---|
| 2019/0197358 A1 | 6/2019 | Madani et al. |
| 2019/0340752 A1 | 11/2019 | Brestel et al. |
| 2020/0085382 A1 | 3/2020 | Taerum et al. |
| 2020/0090350 A1 | 3/2020 | Cho et al. |

FOREIGN PATENT DOCUMENTS

| | | | | |
|---|---|---|---|---|
| WO | WO2017022882 | * | 2/2017 | ........... G06T 7/0012 |
| WO | WO2019217903 | * | 11/2019 | ............... G06K 9/00 |

OTHER PUBLICATIONS

Syeda-Mahmood, Tanveer, et al. "Discriminating normal and abnormal left ventricular shapes in four-chamber view 2D echocardiography." 2014 IEEE 11th International symposium on biomedical imaging (ISBI). IEEE, 2014.

Arbabshirani, Mohammad R., et al. "Advanced machine learning in action: identification of intracranial hemorrhage on computed tomography scans of the head with clinical workflow integration." NPJ digital medicine 1.1 (2018): 1-7.

Chakravarty, Arunava, Divya Jyothi Gaddipati, and Jayanthi Sivaswamy. "Construction of a retinal atlas for macular oct volumes." International Conference Image Analysis and Recognition. Springer, Cham, 2018.

Antal, Bálint, et al. "A two-phase pre-filtering approach to the automatic screening of digital fundus images." 2010 International Conference on Signal Processing and Multimedia Applications (SIGMAP). IEEE, 2010.

* cited by examiner

AI-BASED IMAGE ANALYSIS FOR THE DETECTION OF NORMAL IMAGES

CROSS-REFERENCE TO RELATED APPLICATIONS

The present application claims priority to U.S. Provisional Patent Application No. 63/033,875, titled AI-BASED IMAGE ANALYSIS FOR THE DETECTION OF NORMAL IMAGES (ESPECIALLY FOR MULTI-INDICATION EXAMS), filed Jun. 3, 2020, which is hereby incorporated by reference herein in its entirety.

BACKGROUND

The volume of medical images that need to be processed keeps growing from year to year, which creates an ever-increasing burden on the radiologists tasked with analyzing and interpreting these images. Further, due to conventional medical practices, some types of medical images, such as chest x-rays or chest CT images (e.g., for lung cancer screening), have a high rate of "normals" (i.e., cases without any radiographically visible abnormality). Reviewing normals can take up a substantial amount of radiologists' time, which could be better spent reviewing and analyzing medical images that actually have radiographically visible abnormalities. Therefore, if there were a mechanism to pre-filter normals (especially for types of medical images that tend to have high rates of normals), it could help free radiologists' time to review and analyze abnormal cases that require more detailed interpretation for the purposes of making treatment decisions, providing differential diagnoses, or assessing disease prognoses.

Some radiology practices use technicians to pre-sort abnormal and normal candidate images manually. However, this is still a time-consuming process and technicians' work generally must still be reviewed by a radiologist before a final determination can be made that no abnormality is present. Further, some machine learning algorithms have been developed to assist in pre-screening medical images for radiologists. However, these algorithms likewise have issues. In particular, most machine learning algorithms have been developed to address only one type of finding only (e.g. pulmonary nodules). Therefore, a radiologist still needs to review each medical image for what are commonly known as "incidental findings," which may be clinically relevant and must be reported. For example, a machine learning algorithm configured to identify normal chest exams still has to be aware of any sort of abnormality (e.g., associated with any of the mediastinum, lung fields, heart, ribs, spine, or abdomen). To date, however, most algorithms show <100% performance in negative predictive value even for the index lesion and do not address all of the "incidental findings" that a radiologist would be required to identify. Accordingly, current machine learning algorithms leave some doubt as to whether they can reliably determine that there are no clinically relevant findings within a medical image.

As previously noted, some machine learning algorithms have been developed to assist in pre-screening medical images. For example, a machine learning algorithm for use in triage uses inverse examples (i.e., images highly likely to contain abnormalities which require immediate attention, such as intracranial hemorrhage) to identify abnormal images. As another example, a machine learning algorithm is used to screen pap smears to identify those with no abnormalities and designate such pap smears as "no further review" (NFR). However, the medical practice must still perform a quality control step by the pathologist to overread at least a proportion of the NFRs to monitor performance of the software and manage the risk of false negatives. Therefore, although these machine learning algorithms could generally be helpful, they do not solve the inherent issues of occupying radiologists' time and broad applicability to a wide range of types of medical images and conditions.

Therefore, an AI-based pre-read of images to assess whether the images are "normal," i.e., whether there is an absence of abnormalities, could remedy these issues. Further, AI systems that were additionally configured to identify and provide reports of specific types of abnormal findings could free radiologists' time for truly complex cases (e.g., interventional radiology). Further, real-time screening of medical images could expedite the release of patients from the care facility who might otherwise be referred for advanced imaging before departing.

SUMMARY

Conventional AI algorithms are trained or programmed to detect one specific type of abnormality (e.g., nodules or calcifications) present within medical images. However, in multi-indication exams, such as a chest CT or X-ray, there are more than 500 diseases that can present radiographically on such exams. It would be time- and cost-prohibitive to aggregate lesion-specific algorithms for any of such abnormality. In addition, it will be hard to argue completeness of findings for emerging diseases (e.g. COVID-19).

In one embodiment, the present disclosure is directed to a computer-implemented method for identifying an abnormal medical image, the method comprising: receiving a medical image; segmenting an anatomical structure from the medical image to define a segmented dataset; registering the segmented dataset to a baseline dataset defining a normal anatomical structure; classifying, by an abnormality classifier, whether the anatomical structure within the medical image as either abnormal or normal, wherein the abnormality classifier comprises a machine learning algorithm trained to distinguish between normal and abnormal versions of the anatomical structure in medical images; and based on whether the anatomical structure can be segmented from the medical image, whether the segmented dataset can be registered to the baseline dataset, or a classification associated with the medical image output by the abnormality classifier, flagging the medical image as either normal or abnormal.

In another embodiment, the present disclosure is directed to a computer system for identifying an abnormal medical image, the computer system comprising: a processor; and a memory coupled to the processor, the memory storing instructions that, when executed by the processor, cause the computer system to: receive a medical image, segment an anatomical structure from the medical image to define a segmented dataset, register the segmented dataset to a baseline dataset defining a normal anatomical structure, classify, by an abnormality classifier, whether the anatomical structure within the medical image as either abnormal or normal, wherein the abnormality classifier comprises a machine learning algorithm trained to distinguish between normal and abnormal versions of the anatomical structure in medical images, and based on whether the anatomical structure can be segmented from the medical image, whether the segmented dataset can be registered to the baseline dataset, or a classification associated with the medical image output by the abnormality classifier, flagging the medical image as either normal or abnormal.

FIGURES

The accompanying drawings, which are incorporated in and form a part of the specification, illustrate the embodiments of the invention and together with the written description serve to explain the principles, characteristics, and features of the invention. In the drawings.

DESCRIPTION

Figure 1:
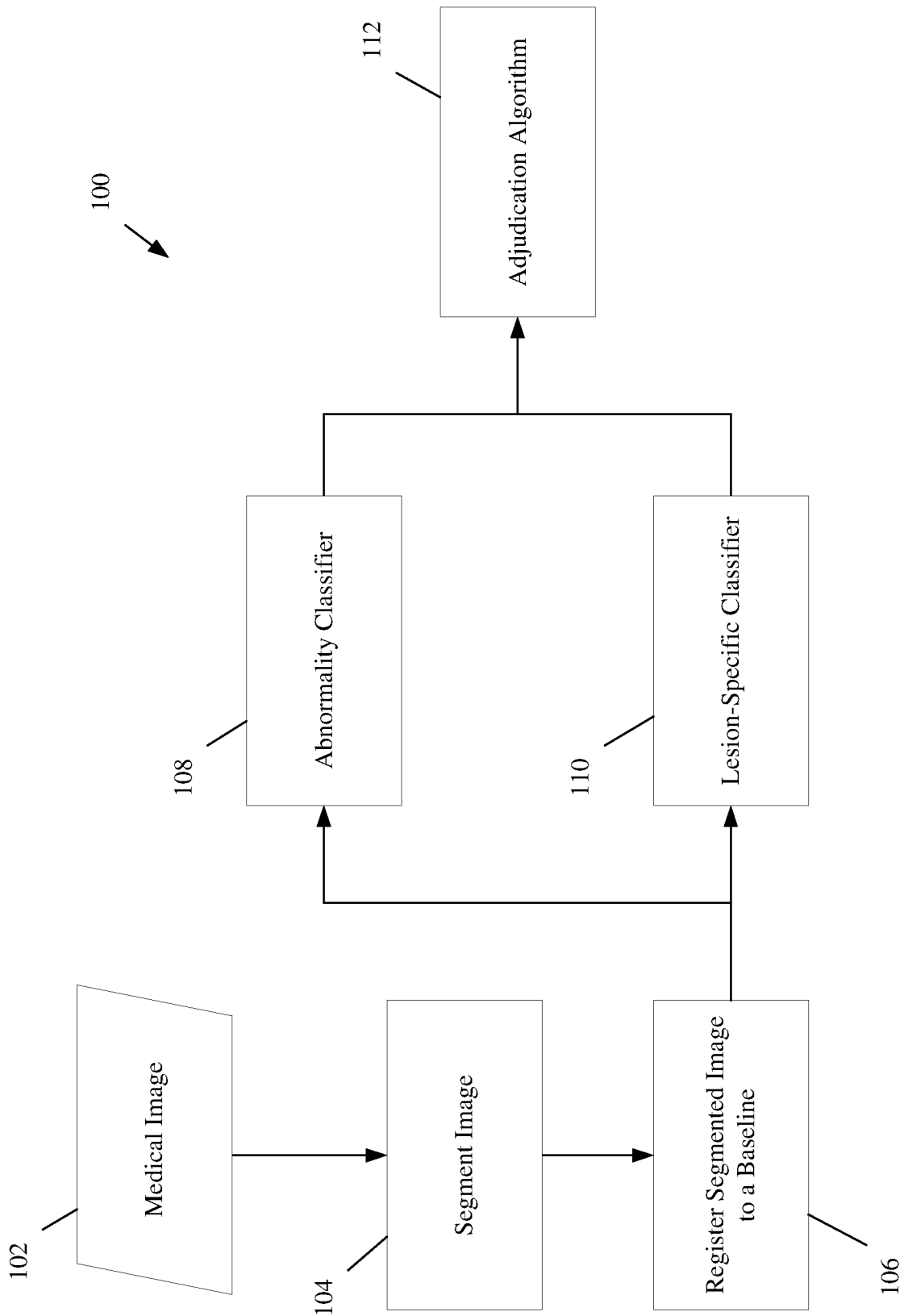
FIG. 1 is a block diagram of an AI system for identifying normal medical images, in accordance with at least one aspect of the present disclosure.

This disclosure is not limited to the particular systems, devices and methods described, as these may vary. The terminology used in the description is for the purpose of describing the particular versions or embodiments only, and is not intended to limit the scope.

As used herein, the terms "algorithm," "system," "module," or "engine," if used herein, are not intended to be limiting of any particular implementation for accomplishing and/or performing the actions, steps, processes, etc., attributable to and/or performed thereby. An algorithm, system, module, and/or engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular algorithm, system, module, and/or engine is, unless otherwise specified, for purposes of convenience of reference and not intended to be limiting to a specific implementation. Additionally, any functionality attributed to an algorithm, system, module, and/or engine may be equally performed by multiple algorithms, systems, modules, and/or engines, incorporated into and/or combined with the functionality of another algorithm, system, module, and/or engine of the same or different type, or distributed across one or more algorithms, systems, modules, and/or engines of various configurations.

As used herein, the term "medical image" can include an image obtained via computed tomography (CT), a magnetic resonance imaging (MRI), positron emission tomography (PET), single-photon emission CT (SPECT), radiography (e.g., X-ray imaging), ultrasonography (i.e., ultrasound imaging), microscopy, optical coherence tomography, photoacoustic imaging, and other biomedical imaging modalities suitable for obtaining images of biological or non-biological structures. Further, a "medical image" can include a three-dimensional image or a two-dimensional image (e.g., a slice of a three-dimensional image).

As used herein, the term "classifier" can include a machine learning algorithm that automatically orders or categorizes data into one or more of a set of classes.

Detecting Normal Anatomical Structures within Medical Images

This disclosure is generally directed to computer-implemented methods and systems for identifying normal images (also referred to as "normals") of organs or other anatomical structures within medical images. The methods and systems described herein could be used as part of a screening process for flagging medical images that require further review by radiologists, for example.

Currently, radiologists spend large percentages of their time reviewing medical images that are completely normal and lack any defects, diseased conditions, or other abnormalities. This is problematic because reviewing normal medical images takes away radiologists' time that they could be spending reviewing truly critical or complex cases (e.g., interventional cases). One way to remedy this problem is to implement a system that provides an AI-based "pre-read" of all of the medical images that the radiologist has been assigned to review to assess and identify normals (i.e., images demonstrating an absence of abnormalities). The system could evaluate the images and autonomously determine whether each particular image is normal (i.e., "no abnormality"). The system could then autonomously draw a conclusion from this evaluation and makes a recommendation, which is communicated automatically to the radiologists and/or the radiologists' image review systems, thus freeing radiologists' time for truly complex cases (e.g., interventional cases). In one embodiment, the automatic communication of the recommendations by the system could be in the form of, for example, (i) a Digital Imaging and Communications in Medicine (DICOM) report that the image does not contained any abnormality and does not require further review, (ii) a submission of the medical image for further evaluation by an ensemble of pathology-specific algorithms, or (iii) a placement of the medical image in a queue for further review by a human radiologist.

Embodiments of the present disclosure are directed to a AI system 100 including an abnormality classifier 108. The abnormality classifier 108 can include one or more algorithms that are each programmed, trained, or otherwise configured to identify a characteristic pattern indicative of one or more classes of abnormalities associated with an anatomical structure (e.g., an organ or organ system) within a medical image 102 that is input to or received by the AI system 100. The abnormality classes that the algorithms are configured to identify can refer to a pattern of structural characteristics demonstrated by or otherwise associated with an anatomical structure that can be viewed within a medical image and are indicative (either alone or in combination with other abnormality classes) of one or more different diseases or conditions. Accordingly, the algorithms can be used to collectively determine whether an anatomical structure is in a normal or baseline state (and, thus, does not require further review or requires only minimal further review by a radiologist) or is in an abnormal state (and, thus, requires further review by a radiologist) based on the presence or lack thereof of the various abnormality classes associated with the anatomical structures in the medical image. The classes of abnormalities that could be detected by the one or more algorithms of the abnormality classifier 108 can include, for example, whether the volume of the anatomical structure is outside of a normative range (e.g., cardiomegaly), whether there has been a focal change in the anatomical structure compared to a prior scan of the anatomical structure (e.g., a new lesion associated with the anatomical structure), a volume change associated with the anatomical structure compared to a prior scan (e.g., a collapsed lung or increased liver volume), a structural distortion associated with the anatomical structure (e.g., a bulging aortic aneurysm), a structural displacement associated with the anatomical structure (e.g., a collapsed lung leading to a displaced trachea), a focal area associated with the anatomical structure that has abnormally high or low attenuation (e.g., low lung attenuation can be indicative of emphysema and high lung attenuation can be indicative of edema, a mass, and other conditions), whether all of the anatomical structures that should be present within the medical image are in fact present, whether there is a deviation from an expected symmetry between anatomical structures (e.g., whether there is a deviation in symmetry between the left and right lungs), whether there is a discontinuity between parts of an anatomical structure (e.g., due to trauma or a laceration), the degree or amount of space occupied by non-organs (e.g., fat or foreign objects), the wall thickness of hollow visceral organs, or added physiological analysis (e.g., blood flow simulations). Each of the aforementioned abnormality classes could be identified by one or multiple algorithms of the abnormality classifier 108.

The AI system 100 can be configured to segment 104 one or more anatomical structures from the medical image 102 using a variety of different image segmentation techniques, such as alpha shapes. Further, the segmented anatomical structures can be identified by the AI system 100 by comparing the segmented structures to models of a normal or baseline version of the anatomical structure. For example, the bony structures in the chest can be segmented in a CT dataset due to their density. If the segmentation process fails, that can be a sign of abnormalities associated with the analyzed anatomical structures. For example, normal bones have a high-density, continuous, smooth surface (e.g., cortical bone) that can generally be segmented relatively easily because it has a very steep density gradient to the surrounding soft tissue. However, if the segmentation algorithm fails because of violation of preconditions associated with this anatomical structure (e.g., if an osteolytic lesion is present, it can disrupt the continuity of the cortical bone, which causes there to be no steep density gradient to the surrounding soft tissue), the anatomical structure can be considered to be potentially abnormal and the dataset may require further review. Once the received medical image 102 has been segmented 104, the AI system 100 can register 106 the segmented dataset to a normal dataset (e.g., a digital representation of "standard" or "normal" anatomy, such as an atlas derived by averaging of a large number of datasets from diverse persons to reflect an "average" anatomy) using, for example, elastic transformation with boundary conditions. If the registration is possible within the boundary conditions, the anatomical structure can be considered to be normal. If registration fails due to the boundary conditions, the anatomical structure can be considered to be potentially abnormal and require review. This approach allows the AI system 100 to immediately exclude a variety of different conditions, such as scoliosis, absence of ribs, and/or additional vertebrae, because the registration process will fail. Accordingly, the AI system 100 need not be trained to individually identify such types of conditions, which is highly beneficial because some of those types of conditions may be extremely rare or unique. Therefore, if the AI system 100 can be configured to exclude such conditions without needing to be explicitly trained to do so, this can obviate the need to acquire sufficient training data to train the AI system 100 to identify the aforementioned conditions and save runtime resources by not requiring that the AI system 100 execute separate algorithms to identify the aforementioned conditions.

In one embodiment, the AI system 100 can comprise multiple abnormality classifiers 108 that are each configured to identify whether a particular anatomical structure is normal. In this embodiment, the AI system 100 can be configured to segment different anatomical structures from the received medical image 102 and analyze the anatomical structures on an individualized basis using the corresponding abnormality classifier 108. For example, in an illustrative embodiment where the AI system 100 has been configured to analyze chest medical images, the AI system 100 could include a first abnormality classifier configured to analyze a right lung, a second abnormality classifier configured to analyze a left lung, and a third abnormality classifier configured to analyze ribs. In such embodiments, the AI system 100 could be programmed to analyze the various anatomical structures in the medical image 102 sequentially, simultaneously, or a combination thereof.

In one embodiment, the AI system 100 can further include a lesion-specific classifier 110. The lesion-specific classifier 110 can include one or more algorithms that are each programmed, trained, or otherwise configured to identify a particular lesion associated with one or more anatomical structures. The one or more algorithms of the lesion-specific classifier 110 could be configured to identify lesions associated with the same or different anatomical structures. The lesion-specific classifier 110 can be used to identify particularly critical injuries or conditions associated with an anatomical structure, such as a hemorrhage. The lesion-specific classifier 110 could, in effect, simulate manual review by a radiologist by seeking to identify particularly important injuries or conditions in order to validate the findings of the abnormality classifier 108 and mitigate the effects of false negatives thereby.

The AI system 100 can further include an adjudication algorithm 112 that is configured to determine whether the received medical image 102 should be labeled as normal or abnormal (and, thus, require further review by a radiologist). In one embodiment, the adjudication algorithm 112 can be programmed to determine that the medical image 102 is abnormal if at least one of the abnormality classifier 108 or the lesion-specific classifier 110 identify the presence of a potential abnormality from one of the abnormality classes that the AI system 100 has been configured to analyze. Further, the adjudication algorithm 112 can be programmed to take a variety of different actions based on the output from the classifiers 108, 110 described above, such as whether the abnormality classifier 108 classified the image as "normal" or "abnormal" or whether the lesion-specific classifier 110 identified a particular lesion within the medical image 102. In some embodiments, the adjudication algorithm 112 could control whether medical images are presented within the radiologist's worklist (e.g., remove normal medical images from the radiologist's worklist or add abnormal medical images to the radiologist's worklist) from and/or flag medical images within a radiologist's worklist in a software platform, as described below in connection with FIG. 2.

In various embodiments, the classifiers 108, 110 described above can be based on or include a variety of different machine learning techniques, algorithms, systems, or models, such as support vector machines, decisions trees (including random forests), neural networks, and/or Bayes' models. In various embodiments, the neural networks could include deep neural networks, such as convolutional neural networks (CNNs), deep reinforcement learning algorithms, residual neural networks (ResNets), dense CNNs (DenseNets), deep belief networks, and/or generative adversarial networks (GANs). In some embodiments, the machine learning systems could be selected based on the abnormality class or lesion type that they are intended to identify. In one embodiment, the abnormality classifier 108 could include an image-to-image network (e.g., a GAN) or a U-Net (i.e., a CNN developed for biomedical image segmentation) trained to make volumetric assessments of an anatomical structure. In one embodiment, the abnormality classifier 108 could include a registration algorithm programmed to make comparisons between the anatomical structure show by a given medical image to a prior scan of the anatomical structure. In one embodiment, the abnormality classifier 108 could include a fully convolutional one-stage object detector (FCOS) trained to detect structural distortions and displacements associated with an anatomical structure. In one embodiment, the abnormality classifier 108 could include an image segmentation algorithm (e.g., an image-to-image network or a U-Net) trained to segment the target anatomical structure and a thresholding algorithm programmed to detect high and/or low attenuation of the anatomical structure. In one embodiment, the abnormality classifier 108 could include a deep reinforcement learning neural network trained to detect the presence and/or absence of an anatomical structure. In one embodiment, the abnormality classifier 108 could include a Siamese neural network trained to determine the symmetry between one or more anatomical structures (e.g., the right and left lungs). In one embodiment, the abnormality classifier 108 could include a GAN trained to subtract age-related effects from an anatomical structure.

In various embodiments, the AI system 100 could be trained using supervised or unsupervised machine learning techniques. For example, the abnormality classifier 108 could be trained with medical images labeled as "normal" or "abnormal" using supervised learning techniques. In this example, the medical images as a whole could be labeled or one or more anatomical structures shown within the medical images could be labeled. In various implementations, the training data could include a variety of different medical images having instance-level annotations with markups (e.g., bounding boxes or labels). The medical images could be, for example, manually labeled by radiologists or medical imaging technicians. Further, the AI system 100 could tested using validation datasets consisting of images curated and annotated for normal, abnormal, and normal variants for a number of different lesions or conditions.

In some embodiments, the classifiers 108, 110 and other algorithms described above are trained, programmed, or otherwise optimized for the highest possible sensitivity, based on cost of specificity. Accordingly, the medical images classified as "normal" may be safely down-prioritized, or even ignored by the physician, without creating a major risk because the AI system 100 is optimized to reduce false positives (i.e., reduce the risk of classifying a potentially abnormal image as a normal image). Accordingly, the "potentially abnormal" datasets may contain many images that are in fact normal, but the tradeoff to ensure that no abnormal images are falsely classified as normal images, while allowing for some normal images to be falsely classified as abnormal images, is ultimately worth the overall time savings. To illustrate of the benefits of the AI system 100 described herein, consider the following prophetic scenario. A radiologist currently reviews 100% of the images with the same priority and diligence, but only approximately 10% of the images reveal any true abnormality. Therefore, the radiologist's time spent reviewing 90% of the images is essentially wasted (or at least could be better spent on reviewing the abnormal images). With the AI system 100 described herein, the radiologist may instead only look at 50% of the images (because the AI system 100 can identify a large number of the received normal medical images and remove them from the radiologist's queue), but of these 20% (i.e., 10% of the total amount of images) are abnormal. Therefore, the AI system 100 saves 50% of the radiologist's time. Conversely, a higher rate of "abnormal" classifications does not do much harm because even reviewing 55% of images is only a little more work for the radiologist. However, if a classification system produced false "normal" classifications, that would break the function of the entire system because then the radiologists would be required to review the "normal" images with the same diligence in order to confirm the classification system's identification.

Figure 2:
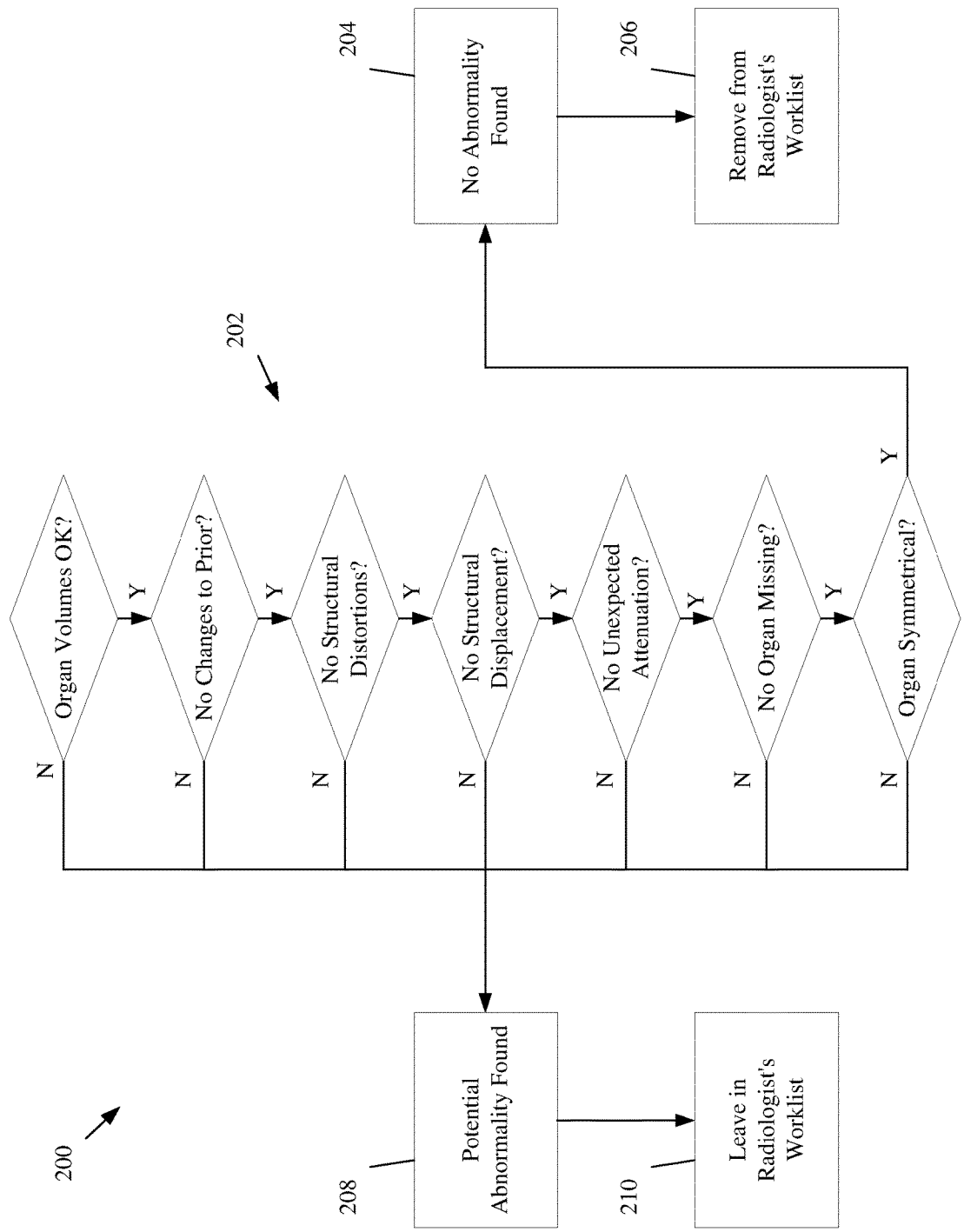
FIG. 2 is a logic flow diagram of a process for analyzing medical images within a radiologist's worklist using the AI system of FIG. 1, in accordance with at least one aspect of the present disclosure.

In one embodiment, AI system 100 could be incorporated into a computer system implementing a workflow queue for radiologists, such as the workflow 200 illustrated in FIG. 2, for example. For example, the AI system 100 could be integrated into or configured to function in conjunction with a picture archiving and communication system (PACS), a radiology information system (RIS), a clinical information system (CIS), and/or other software platforms or tools. The AI system 100 can be configured to function in accordance with a variety of different information standards, such as DICOM. In one embodiment, the AI system 100 could be configured to determine 202 whether an anatomical structure shown within a medical image has an abnormality from one or more abnormality classes (e.g., whether an organ volume is within thresholds, whether there have been no changes to an organ compared to a prior scan, or whether there are any structural distortions or displacements for the organ), as described above. If all of the abnormality classes are negative, the AI system 100 can determine 204 that no abnormality has been found within the medical image. In one embodiment, the AI system 100 could accordingly remove 206 the medical image from the radiologist's worklist (i.e., queue of medical images to review). If at least one of the abnormality classes are positive, the AI system 100 can determine 208 that a potential abnormality has been found within the medical image and leave 210 the medical image in the radiologist's worklist. In one embodiment, the AI system 100 could further add the medical image to the radiologist's worklist to be reviewed, flag the medical image for review by the radiologist, and/or indicate the type of abnormality that was identified by the AI system 100 within the image.

In one embodiment, the abnormality classifier 108 and the lesion-specific classifier 110 can function as an ensemble to facilitate the ability to rule out normal medical images that do not require any further review by radiologists. The ensemble identifies normals and manages the risk of false negatives (i.e., by seeking to identify particularly critical lesions) in order to provide an optimal balance of benefit and risk for the patient, physician, and care provider. To date, no available or approved medical image prescreening systems are able to provide the functional and clinical utility described above with respect to the AI system 100. Accordingly, the AI system 100 could, in some applications, autonomously report normal, normal variant, and/or abnormal medical images, characterize the abnormal findings, and manage the risk of false positives by selecting appropriate lesions to be monitored by the lesion-specific classifier 110.

Medical Imaging System Architecture

Figure 3:
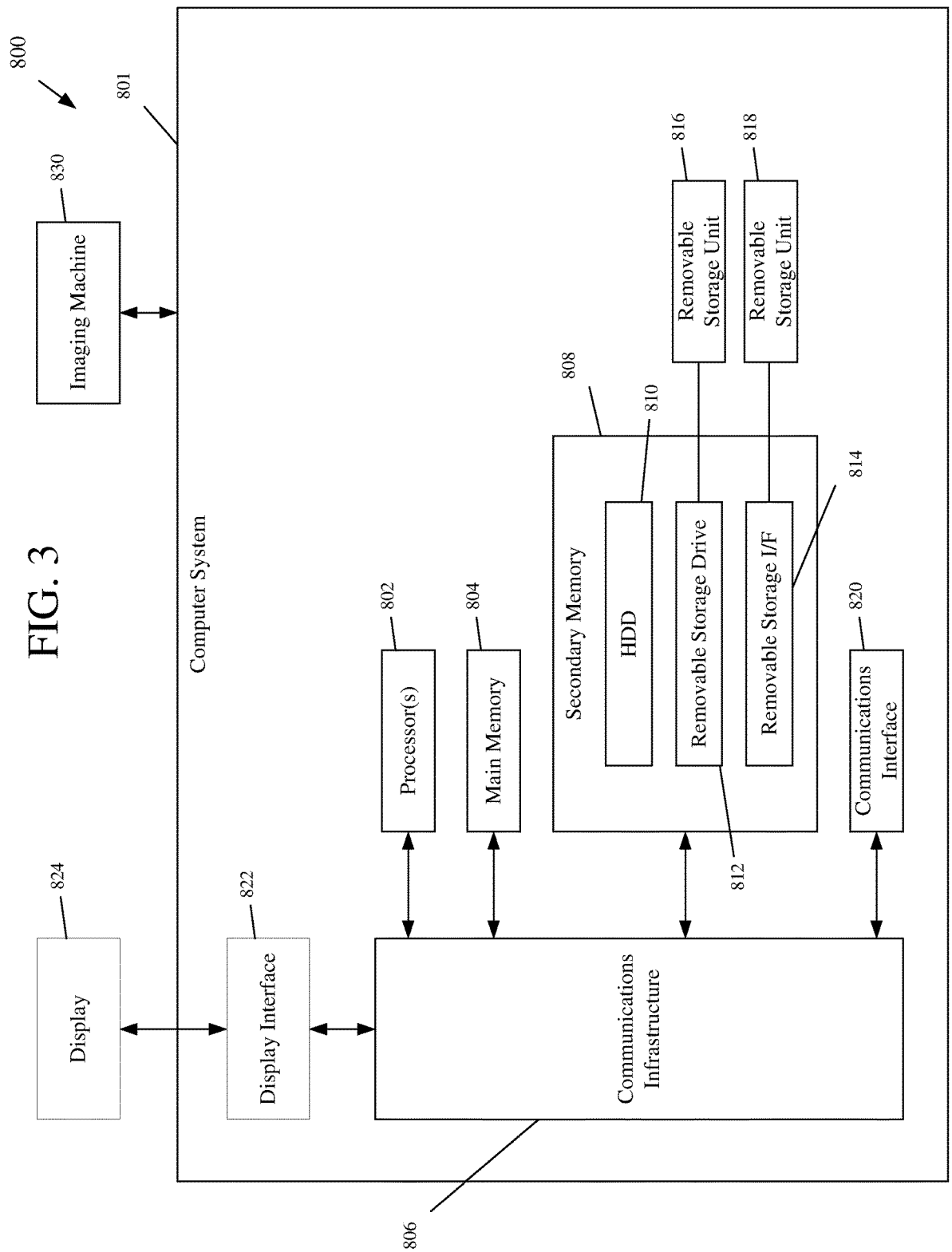
FIG. 3 is a block diagram of a medical imaging system, in accordance with at least one aspect of the present disclosure.

In some embodiments, the systems and techniques described above can be implemented in or by a medical imaging system, such as the medical imaging system 800 illustrated in FIG. 3.

FIG. 3 is an architecture diagram of medical imaging system 800 that may be used in some embodiments. As noted above, the medical imaging system 800 can include a computer system 801 and an imaging machine 830 (e.g., an MRI machine). The computer system 801 may include one or more processors 802. Each processor 802 is connected to a communication infrastructure 806 (e.g., a communications bus, cross-over bar, or network). The processor(s) 802 can include a CPU, a GPU, an AI accelerator, and/or a variety of other processor types. Computer system 801 may include a display interface 822 that forwards graphics, text, and other data from the communication infrastructure 806 (or from a frame buffer, not shown) for display on the display unit 824.

Computer system 801 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer system 801. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer system 801.

Computer system 801 may also include a communications interface 820. Communications interface 820 allows software and data to be transferred between computer system 801 and external devices. Examples of communications interface 820 may include a modem, Ethernet card, wireless network card, a Personal Computer Memory Card International Association (PCMCIA) slot and card, or the like. Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, a hard disk installed in hard disk drive 810, or removable storage unit 816. These computer program products provide software to computer system 801. Computer programs (also referred to as computer control logic) may be stored in main memory 804 and/or secondary memory 808. Computer programs may also be received via communications interface 820. Such computer programs, when executed by a processor, enable the computer system 801 to perform the features of the methods discussed herein. For example, main memory 804, secondary memory 808, or removable storage units 816 or 818 may be encoded with computer program code (instructions) for performing operations corresponding to various processes disclosed herein.

It is understood by those familiar with the art that the system described herein may be implemented in hardware, firmware, or software encoded (e.g., as instructions executable by a processor) on a non-transitory computer-readable storage medium.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

Aspects of the present technical solutions are described herein with reference to flowchart illustrations and/or block diagrams of methods, apparatuses (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present technical solutions. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action can be said to be "in response to" a first action independent of whether the second action results directly or indirectly from the first action. The second action can occur at a substantially later time than the first action and still be in response to the first action. Similarly, the second action can be said to be in response to the first action even if intervening actions take place between the first action and the second action, and even if one or more of the intervening actions directly cause the second action to be performed. For example, a second action can be in response to a first action if the first action sets a flag and a third action later initiates the second action whenever the flag is set.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A computer-implemented method for identifying an abnormal medical image, the method comprising:
   receiving a medical image;
   segmenting an anatomical structure from the medical image to define a segmented dataset;
   registering the segmented dataset to a baseline dataset defining a normal anatomical structure;
   classifying, by an abnormality classifier, whether the anatomical structure within the medical image as either abnormal or normal, wherein the abnormality classifier comprises a machine learning algorithm trained to distinguish between normal and abnormal versions of the anatomical structure in medical images; and
   based on whether the anatomical structure can be segmented from the medical image, whether the segmented dataset can be registered to the baseline dataset, or a classification associated with the medical image output by the abnormality classifier, flagging the medical image as either normal or abnormal; and
   based on whether the medical image has been flagged as normal or abnormal, controlling whether the medical image is in a worklist associated with a radiologist, wherein the worklist is associated with a software platform, the software platform comprising at least one of a picture archiving and communication system, a radiology information system, or a clinical information system.

2. The method of claim 1, further comprising:
   classifying, by a lesion-specific classifier, whether the anatomical structure exhibits a lesion, wherein the lesion-specific classifier comprises a second machine learning algorithm trained to identify the lesion in medical images; and
   wherein flagging the medical image as either normal or abnormal is further based on whether the lesion-specific classifier has identified the lesion in the medical image.

3. The method of claim 2, wherein the lesion-specific classifier comprises at least one of a support vector machine, a decisions tree, a neural network, or a Bayes' model.

4. The method of claim 1, wherein the medical image comprises at least one of a computed tomography (CT) image, a magnetic resonance imaging image, a positron emission tomography image, a single-photon emission CT image, an X-ray image, an ultrasound image, an optical coherence tomography image, or a photoacoustic image.

5. The method of claim 1, wherein the abnormality classifier comprises at least one of a support vector machine, a decisions tree, a neural network, or a Bayes' model.

6. A computer system for identifying an abnormal medical image, the computer system comprising:
   a processor; and
   a memory coupled to the processor, the memory storing instructions that, when executed by the processor, cause the computer system to:
   receive a medical image,
   segment an anatomical structure from the medical image to define a segmented dataset,
   register the segmented dataset to a baseline dataset defining a normal anatomical structure,
   classify, by an abnormality classifier, whether the anatomical structure within the medical image as either abnormal or normal, wherein the abnormality classifier comprises a machine learning algorithm trained to distinguish between normal and abnormal versions of the anatomical structure in medical images, and
   based on whether the anatomical structure can be segmented from the medical image, whether the segmented dataset can be registered to the baseline dataset, or a classification associated with the medical image output by the abnormality classifier, flagging the medical image as either normal or abnormal; and
   wherein the memory stores further instructions that, when executed by the processor, cause the computer system to:
   based on whether the medical image has been flagged as normal or abnormal, remove the medical image from a worklist associated with a radiologist, wherein the worklist is associated with a software platform, the software platform comprising at least one of a picture archiving and communication system, a radiology information system, or a clinical information system.

7. The computer system of claim 6, further comprising an imaging machine, wherein the medical image is received from the imaging machine.

8. The computer system of claim 6, wherein the abnormality classifier comprises at least one of a support vector machine, a decisions tree, a neural network, or a Bayes' model.

9. The computer system of claim 6, wherein the memory stores further instructions that, when executed by the processor, cause the computer system to:
   classify, by a lesion-specific classifier, whether the anatomical structure exhibits a lesion, wherein the lesion-specific classifier comprises a second machine learning algorithm trained to identify the lesion in medical images; and
   wherein flagging the medical image as either normal or abnormal is further based on whether the lesion-specific classifier has identified the lesion in the medical image.

10. The computer system of claim 9, wherein the lesion-specific classifier comprises at least one of a support vector machine, a decisions tree, a neural network, or a Bayes' model.

11. The computer system of claim 6, wherein the medical image comprises at least one of a computed tomography (CT) image, a magnetic resonance imaging image, a positron emission tomography image, a single-photon emission CT image, an X-ray image, an ultrasound image, an optical coherence tomography image, or a photoacoustic image.

* * * * *